US011219477B2

(12) United States Patent
Biedermann et al.

(10) Patent No.: US 11,219,477 B2
(45) Date of Patent: Jan. 11, 2022

(54) INSTRUMENT FOR ATTACHING TO A BONE ANCHOR AND INSTRUMENT FOR USE IN DISTRACTION AND/OR RETRACTION, IN PARTICULAR FOR ORTHOPEDIC SURGERY OR NEUROSURGERY, MORE SPECIFICALLY FOR SPINAL SURGERY

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 153 days.

(21) Appl. No.: 16/577,961

(22) Filed: Sep. 20, 2019

(65) Prior Publication Data
US 2020/0093529 A1 Mar. 26, 2020

Related U.S. Application Data

(60) Provisional application No. 62/734,485, filed on Sep. 21, 2018.

(30) Foreign Application Priority Data

Sep. 21, 2018 (EP) .................................... 18196118

(51) Int. Cl.
*A61B 17/88* (2006.01)
*A61B 17/02* (2006.01)
(Continued)

(52) U.S. Cl.
CPC ...... *A61B 17/8872* (2013.01); *A61B 17/0206* (2013.01); *A61B 17/0218* (2013.01);
(Continued)

(58) Field of Classification Search
CPC ............ A61B 17/8872; A61B 17/0206; A61B 17/7077; A61B 17/7079; A61B 2017/00353
See application file for complete search history.

(56) References Cited

U.S. PATENT DOCUMENTS 8,636,655 B1   1/2014  Childs
9,307,972 B2 * 4/2016  Lovell ................ A61B 17/7077
(Continued)

FOREIGN PATENT DOCUMENTS

DE   10 2016 110706 A1   12/2017
EP      2 934 354 A1     10/2015
(Continued)

OTHER PUBLICATIONS

Extended European Search Report for Application No. 18196118.6, dated Mar. 14, 2019, 9 pages.

*Primary Examiner* — Kevin T Truong
*Assistant Examiner* — Tracy L Kamikawa
(74) *Attorney, Agent, or Firm* — Lewis Roca Rothgerber Christie LLP

(57) ABSTRACT

An instrument configured to attach to a bone anchoring element during surgery includes an elongate portion and an end portion having a first side and an opposite second side, where the elongate portion extends away from the first side, and where an opening is defined at the second side to accommodate at least a portion of a head of the bone anchoring element. The opening of the end portion has a first section sized to permit insertion and removal of the head therethrough, and a second section forming a seat for the
(Continued)

head. When the head is held in the seat, the seat prevents removal of the head through the opening, while the head is movable unobstructedly from the second section back towards the first section.

17 Claims, 15 Drawing Sheets

(51) Int. Cl.
  *A61B 17/70* (2006.01)
  *A61B 1/32* (2006.01)
  *A61B 17/00* (2006.01)
  *A61B 17/3211* (2006.01)
  *A61B 17/92* (2006.01)
(52) U.S. Cl.
  CPC ............ *A61B 17/7077* (2013.01); *A61B 1/32* (2013.01); *A61B 2017/00353* (2013.01); *A61B 2017/0256* (2013.01); *A61B 2017/32113* (2013.01); *A61B 2017/925* (2013.01)

(56) References Cited

U.S. PATENT DOCUMENTS

| | | |
|---|---|---|
| 9,414,828 B2 * | 8/2016 | Abidin .................. A61F 2/4611 |
| 2016/0106408 A1 | 4/2016 | Ponmudi et al. |
| 2017/0143323 A1 | 5/2017 | Cryder et al. |

FOREIGN PATENT DOCUMENTS

| | | |
|---|---|---|
| EP | 3 023 065 A1 | 5/2016 |
| WO | WO 2015/137976 A1 | 9/2015 |

* cited by examiner

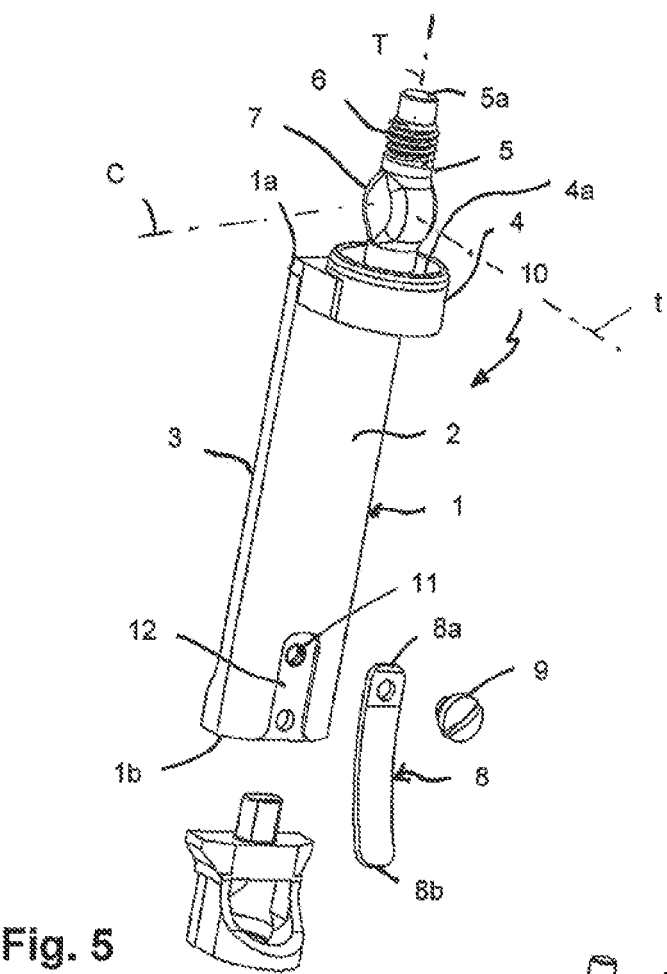
Fig. 5
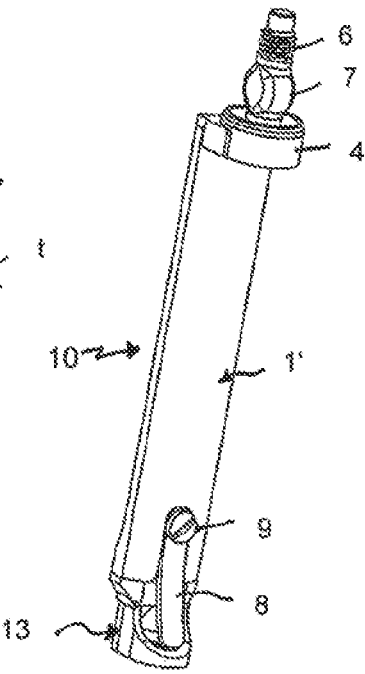 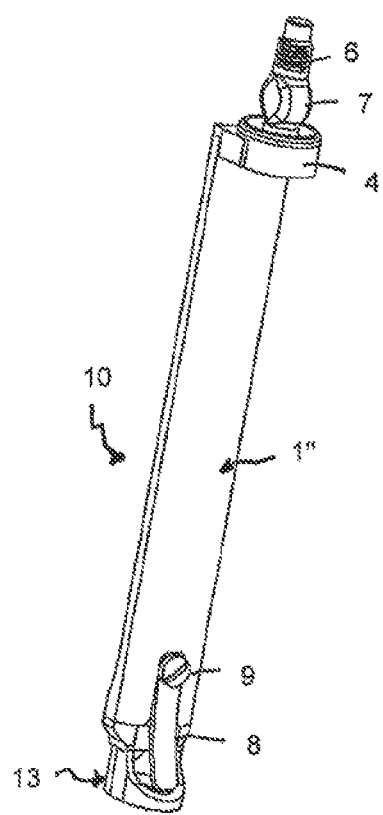
Fig. 6a  Fig. 6b  Fig. 6c

INSTRUMENT FOR ATTACHING TO A BONE ANCHOR AND INSTRUMENT FOR USE IN DISTRACTION AND/OR RETRACTION, IN PARTICULAR FOR ORTHOPEDIC SURGERY OR NEUROSURGERY, MORE SPECIFICALLY FOR SPINAL SURGERY

CROSS-REFERENCE TO RELATED APPLICATION(S)

The present application claims priority to and the benefit of U.S. Provisional Patent Application No. 62/734,485, filed Sep. 21, 2018, the contents of which are hereby incorporated by reference in their entirety, and claims priority from European Patent Application EP 18 196 118.6, filed Sep. 21, 2018, the contents of which are hereby incorporated by reference in their entirety.

BACKGROUND

Filed

The application relates to an instrument for attaching to a bone anchor, more specifically to a retractor blade for attaching to a bone anchor, and to an instrument for use in distraction and/or retraction, in particular for orthopedic surgery or neurosurgery, more specifically for spinal surgery.

Description of Related Art

Distraction and compression steps during spinal surgery are well-known in the art. For example, in the case of single or multilevel discectomies, cages, pedicle screws and rods are often used for providing stability to the spinal segments. In order to remove an intervertebral disk and to insert a cage into the intervertebral space the vertebrae are distracted, i.e., their distance relative to each other is increased. This is accomplished by using, for example, distraction pliers that engage two adjacent pedicle screws along a rod captured therein and spread them apart from each other. Thereby, the intervertebral space is enlarged.

It may also be necessary to retract soft tissue during the surgical steps using retractor blades. Documents DE 10 2016 110 706 A1 and US 2016/0106408 A1 describe instruments for use in spinal surgery that can be used for distraction and tissue retraction.

SUMMARY

In minimally invasive surgery (MIS), only small incisions are made and therefore, the available space for surgical manipulations is reduced. This is also the case in other fields of spinal surgery, such as cervical spinal surgery or pediatric spinal surgery.

In MIS, visibility of the surgical site is very limited. Hence, it is important that an instrument is easy to handle even under restricted visibility and limited available space.

Moreover, known techniques for distraction and/or retraction in some cases may involve difficulties in attaching or holding the instruments while performing distraction and/or retraction steps.

It is an object of the invention to provide an improved instrument, more specifically a retractor blade for attaching to a bone anchor, and to an instrument for distraction and/or tissue retraction, in particular for orthopedic surgery or neurosurgery, more specifically for spinal surgery.

According to an embodiment of the invention, an instrument for attaching to a bone anchor includes an elongate portion and an end portion for connecting to a head of a bone anchoring element. The end portion is configured to accommodate at least a portion of the head of the bone anchoring element, and includes a first section configured to permit placement of the instrument onto and removal of the instrument from the head, and that further includes a second section that is configured to prevent removal of the instrument from the head.

In a specific aspect, the instrument is a retractor blade. The retractor blade is not limited to the function of retracting soft tissue or muscles, but the term retractor blade also includes the possibilities that the blade can be adapted to be used for distraction, compression, and other steps in surgery.

An advantage of the instrument, and more specifically the retractor blade, is that it is attachable to a preferably spherically-shaped head of a bone anchoring element. Hence, the surgical steps can be carried out while the instrument that is used for carrying out the surgical steps is safely attached. Also, the visibility at the surgical site is improved if the retractor blade is attachable to a head of a bone anchoring element that protrudes out of the bone, compared to the case in which a polyaxial receiving part is connected to the bone anchoring element.

According to a further aspect, an instrument for distraction and/or retraction includes at least two retractor blades that are mountable to respective arms attached to a frame, such as a positioning rod.

The retractor blade or the instrument, respectively, can be attached to the heads, in particular to the spherically-shaped heads of pedicle screws or other bone screws that are inserted into the pedicles or bone parts, prior to mounting the receiving parts for polyaxially connecting the screws to a rod.

Furthermore, the retractor blade is designed such that the step of locating the head of the screw and attaching the retractor blade to the head is more easily facilitated. Therefore, the retractor blade or the instrument is suitable even under surgical conditions with poor visibility and little available space, such as in the case of minimally invasive surgery. Moreover, the attachment is also secure, where unwanted detachment is impeded. However, the retractor blade and instrument is not limited to MIS, but can also be used for open surgery.

According to an aspect, the attachment of the head to the end portion of the retractor blade is assisted by a spring force. Thereby, the retractor blade is pushed into a position in which removal is prevented or impeded. This considerably simplifies the attachment step. The attachment step may include a vertical and thereafter a lateral movement of the end portion of the retractor blade relative to the head. The detachment step may include a lateral movement and thereafter a vertical movement of the end portion of the retractor blade relative to the head. This increases the safety against inadvertent removal of the retractor blade.

According to another aspect, the retractor blades are mounted to the arms of the instrument in such a manner that blade portions of the first retractor blade and the second retractor blade form a predefined angle, for example an angle of about 90° or exactly 90°. The predetermined angle formed by the retractor blades ensures that soft tissue can be retracted in a simple manner to enlarge the space and enhance the visibility at the surgical site.

According to another aspect, the retractor blade includes a seat for pivotably holding the head. This allows adapting of the orientation of the retractor blade to positions of the screw. In a still further aspect, the retractor blade is pivotable in a single plane relative to the arm of the instrument to allow adjustments of the position of the arm and the frame with respect to the retractor blade. The retractor blade may be locked relative to the arm at a desired angle. This allows adapting of the orientation of the retractor blade relative to the arm to cope with varying geometrical situations at the surgical site.

According to a further aspect, the arms of the instrument can assume a straight configuration or an angled configuration, each of which may be locked. This allows the frame to assume an angle with respect to a plane defined by the portions of the arms, respectively, that are mounted to the retractor blades. By means of this, the frame can be held at a position that is closer to a patient's body during surgery.

According to a further aspect, a third retractor blade is provided for the instrument that may be arranged on the frame between the arms and that may be movable in a direction substantially perpendicular to the direction in which the arms can move relative to each other on the frame. By means of this, soft tissue can be retracted and urged away from the first and second retractor blades.

According to a further aspect, at least the first and second retractor blades, and preferably also the third retractor blade, include blade portions that can be interchanged with other blade portions of different sizes, in particular of different lengths. This permits adapting of the instrument to specific situations and dimensions at the surgical site. The retractor blades can also be monolithic. According to a still further aspect, the length of the retractor blades is adjustable.

Embodiments of the invention also include bone anchoring elements having a shank for anchoring in bone and a head, wherein the head is preferably a spherical segment-shaped head.

A method for distraction and/or retraction, in particular for orthopedic surgery or neurosurgery, more specifically for spinal surgery, includes the steps of inserting shanks of a first and a second bone anchoring element in bone, for example in the pedicles of vertebrae, mounting the first retractor blade to a head of the first bone anchoring element by inserting the head into an end portion of the first retractor blade, mounting the second retractor blade to a head of the second bone anchoring element by inserting the head into an end portion of the second retractor blade, attaching a first arm to the first retractor blade and a second arm to the second retractor blade, wherein the first and the second arms are mounted on a frame, and optionally attaching a third retractor blade to the frame.

In an optional additional step, the retractor blades are pivoted in a single plane with respect to the arms and may optionally be fixed at a specific pivot angle. The method may further include a step of distracting two vertebrae by moving the first retractor blade relative to the second retractor blade, thereby also retracting soft tissue with blade portions of the retractor blades.

After distraction and retraction steps, the instrument is removed from the bone anchoring elements. On each bone anchoring element, a receiving part for polyaxially coupling the bone anchoring element to a rod is mounted onto the head of the bone anchoring element. Such receiving parts and a method of mounting them to a bone anchoring element are disclosed, for example, in US 2018/0036039 A1 or in US 2014/0236239 A1, the contents of which are incorporated herein by reference in their entirety.

The first retractor blade and the second retractor blade can also synonymously be designated as a first distractor blade and a second distractor blade. Their function may be retraction of soft tissue and/or distraction of vertebrae or other bone parts.

The invention is not limited to the instrument for attaching to a bone anchor being a retractor blade. The instrument can be used in general for providing attachment to a bone anchor in the course of manipulation during surgery.

BRIEF DESCRIPTION OF THE DRAWINGS

Further features and advantages of the invention will become apparent from the description of embodiments by means of the accompanying drawings. In the drawings:

FIG. 5 shows a perspective exploded view of a retractor blade of the instrument of FIGS. 1 and 2.

FIGS. 6a to 6c show perspective views of different embodiments of retractor blades with blade portions having different lengths.

DETAILED DESCRIPTION

Figure 1:
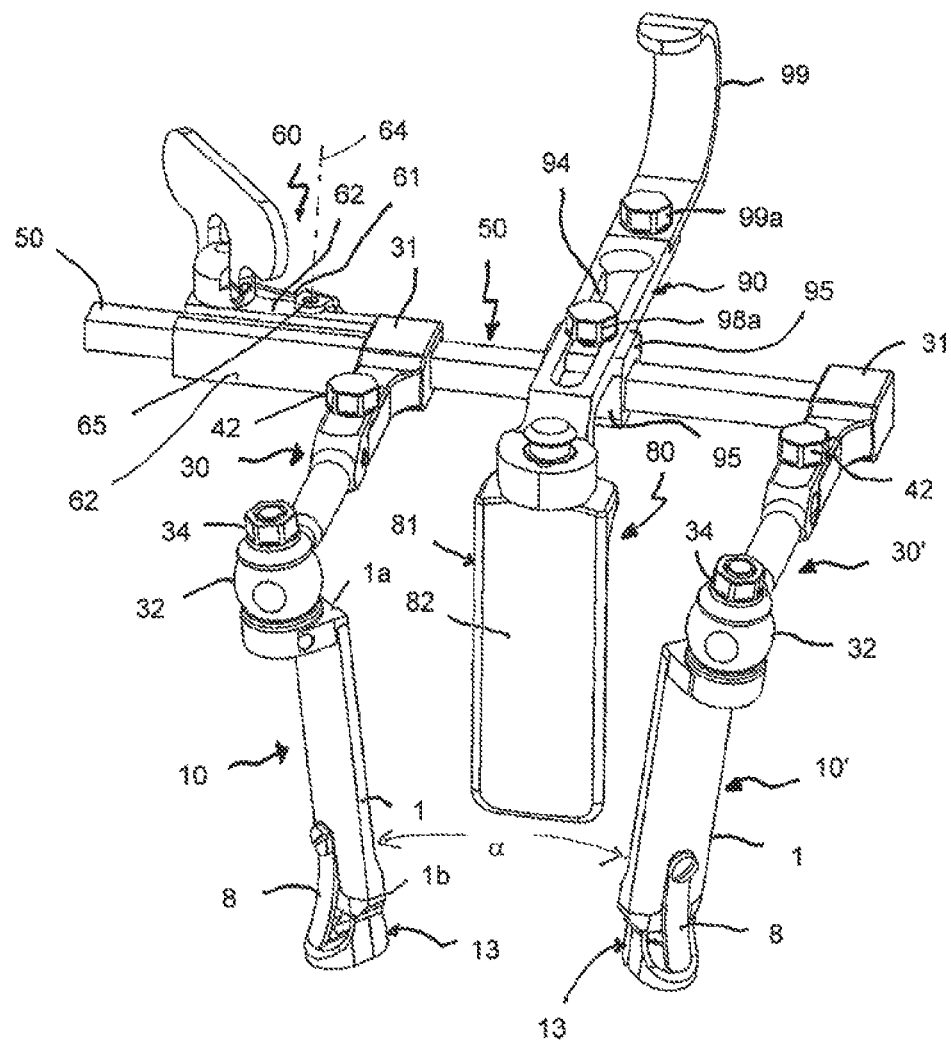
FIG. 1 shows a perspective view of an embodiment of an instrument for attaching to a bone anchor in the form of a retractor blade.
Figure 2:
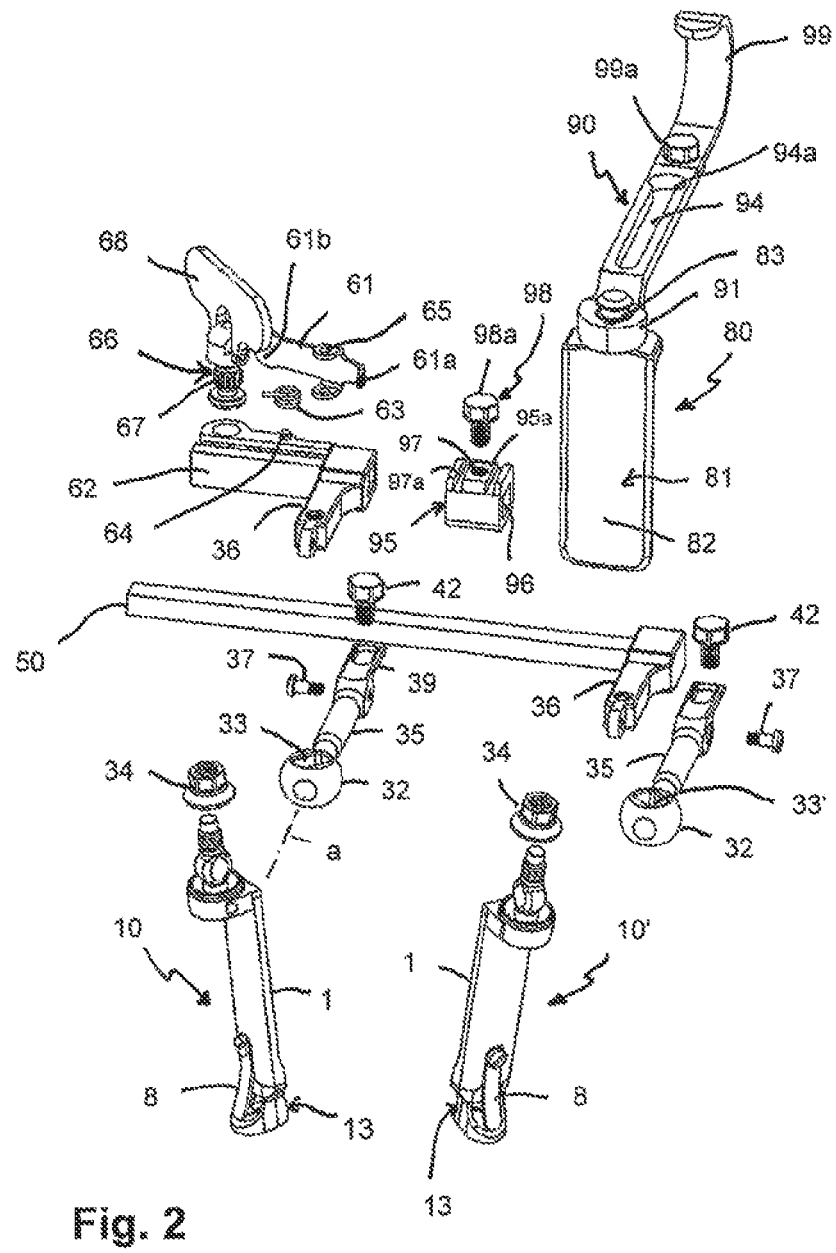
FIG. 2 shows a perspective exploded view of the instrument of FIG. 1.
Figure 3:
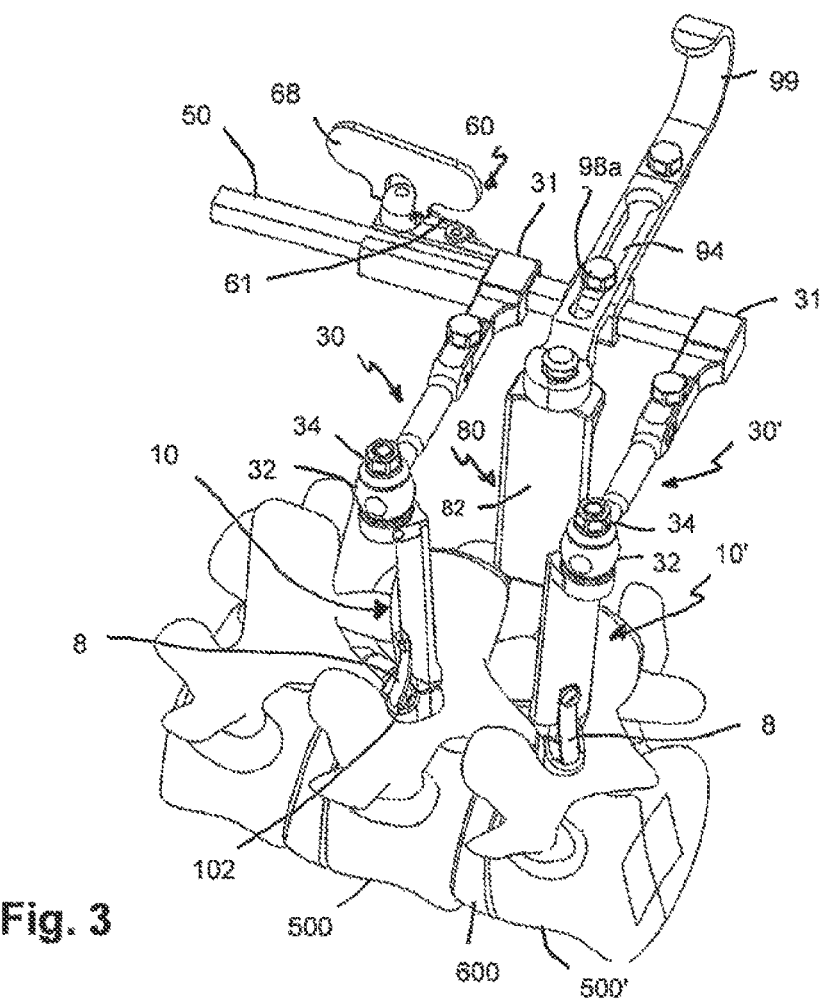
FIG. 3 shows the instrument of FIGS. 1 and 2 attached to bone anchoring elements in the form of pedicle screws inserted into vertebrae.
Figure 4:
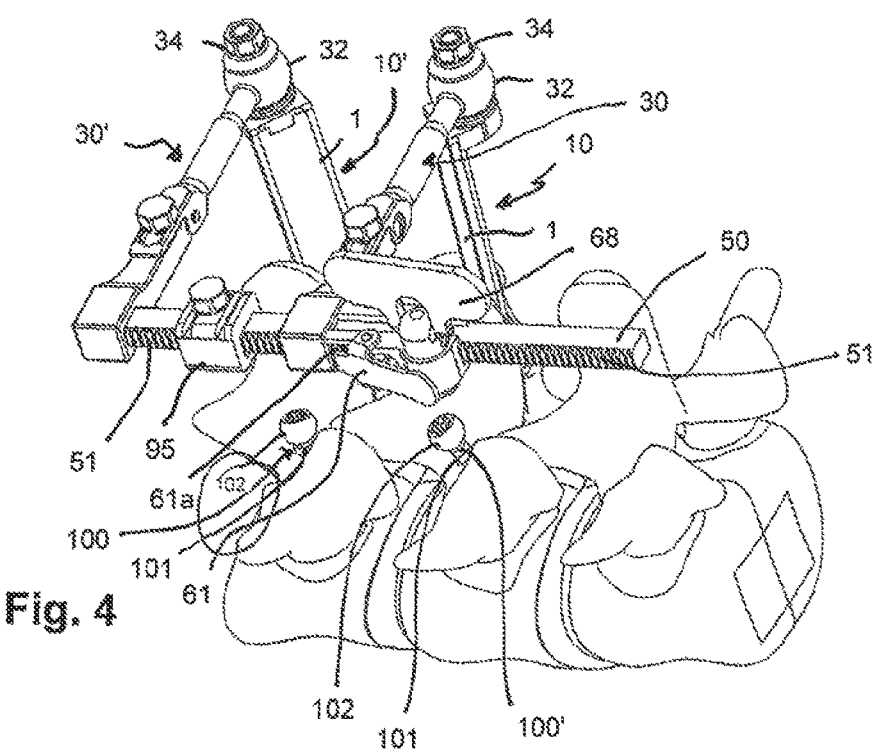
FIG. 4 shows a perspective view of the instrument of FIG. 3, seen from an opposite side of the spinal column.
Figure 7:
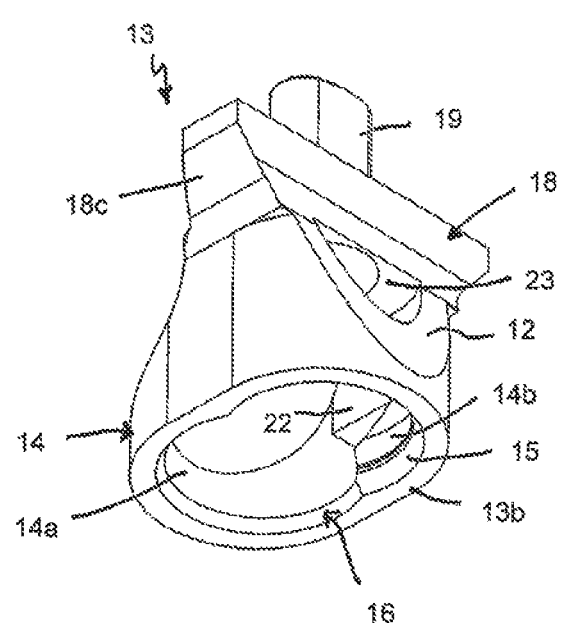
FIG. 7 shows a perspective view from a bottom of an end portion of the retractor blade of FIGS. 5 and 6a to 6c.
Figure 8:
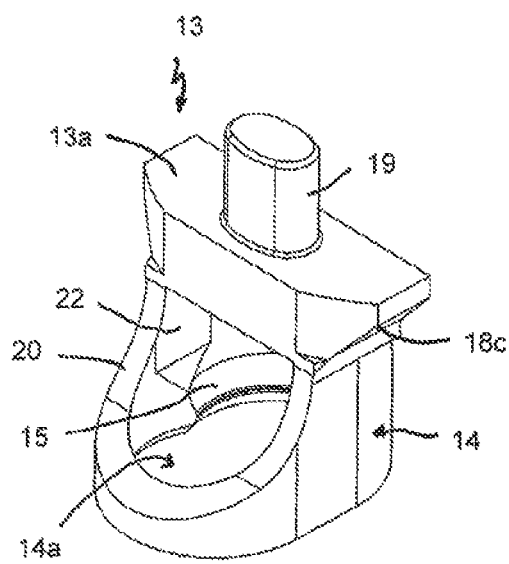
FIG. 8 shows a perspective view from a top of the end portion of FIG. 7.
Figure 9:
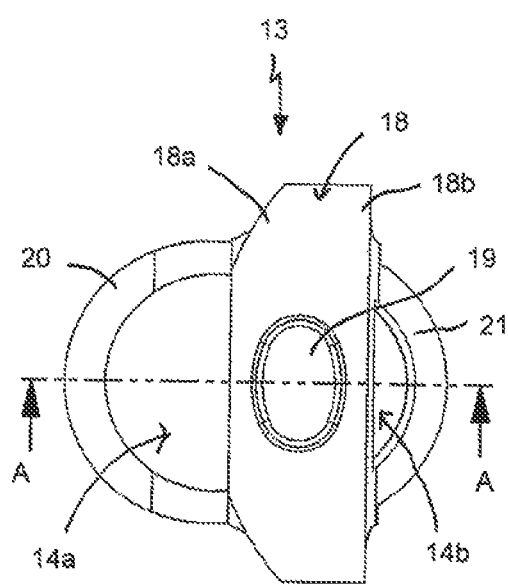
FIG. 9 shows a top view of the end portion of FIGS. 7 and 8.
Figure 10:
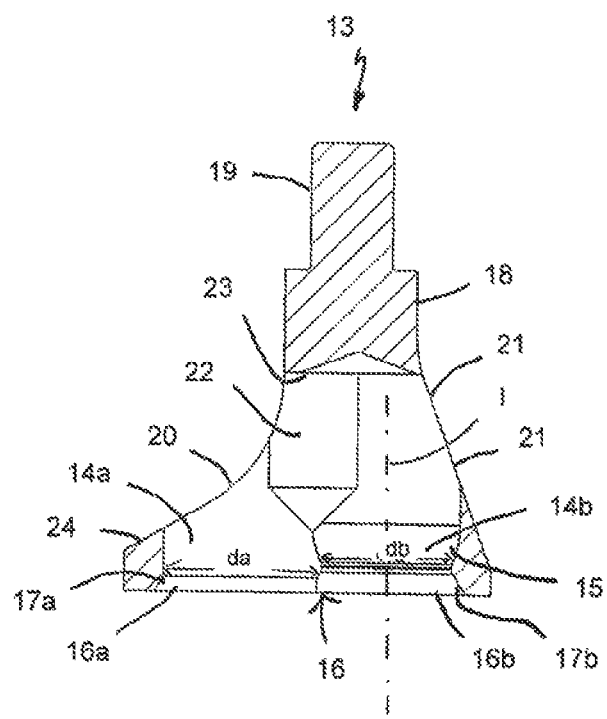
FIG. 10 shows a cross-sectional view of the end portion of FIGS. 7 to 9, the cross-section taken along line A-A in FIG. 9.

Referring to FIGS. 1 to 4, an instrument according to an embodiment of the invention includes a first retractor blade 10 and a second retractor blade 10' that are configured to be connected to bone anchoring elements, for example, bone anchoring elements 100, 100' as shown in FIGS. 3 and 4. The retractor blades 10, 10' shown with the instrument each forms an embodiment of an instrument itself for attaching to a bone anchor, according to aspects of the invention.

Each bone anchoring element 100, 100' includes a shank 101 that is configured to be anchored in bone, for example in the pedicle of a vertebra, and which may be threaded, and a head 102 that has preferably a spherically-shaped outer surface portion. The first retractor blade 10 and the second retractor blade 10' are connectable to a first arm 30 and a second arm 30', respectively, which are attached to a frame that may be a positioning rod 50, that permits positioning of the first and second arms 30, 30' relative to each other. In the embodiment shown, the second arm 30' is fixedly mounted with a first mounting portion 31 to an end of the positioning rod 50. The first arm 30 is slideably mounted with its first mounting portion 31 on the positioning rod. A displacement mechanism 60 is provided for displacing the first arm 30 along the positioning rod 50. For connecting the first and the second retractor blades 10, 10' to the first and the second arms 30, 30', respectively, second mounting portions 32 are provided.

Moreover, a third retractor blade 80 can be mounted to the positioning rod 50, for example, between the first arm 30 and the second arm 30'.

As can be seen in particular in FIGS. 1 and 3 to 4, the first arm 30 and the second arm 30' extend substantially perpendicularly to the positioning rod 50, towards or away from the same side of the positioning rod 50. The first retractor blade 10 and the second retractor blade 10' respectively extend away from the first arm 30 and the second arm 30' towards the same side or direction, and form an angle of substantially 90°, preferably 90°, with a plane spanned by the positioning rod 50 and the arms 30, 30' when they are in a straight configuration.

The first and second retractor blades 10, 10' are identical. The retractor blades will be described with additional reference to FIGS. 5 to 10, referring only to the first retractor blade 10. The first retractor blade 10 includes an elongate portion in the form of a blade portion 1 that has a substantially elongate rectangular contour with a rear side 2 and a front side 3 opposite to the rear side 2. The rear side 2 may be flat or slightly convex and the front side 3 may be flat or slightly concave. If the rear side 2 and the front side 3 are convex or concave, respectively, a smooth retraction of soft tissue may be possible with reduced risk of injuring the tissue. The blade portion 1 includes an upper end 1a that is directed towards the arm 30 and an opposite lower end 1b. From the upper end 1a, an attachment portion 4 extends substantially perpendicularly to a longitudinal direction of the elongate blade portion 1. The attachment portion 4 may have a circular segment-shaped outer contour. From the center of the attachment portion, a post 5 extends away from the upper end 1a of the blade portion 1. The post 5 may have a threaded portion 6 that may be provided at a distance from the free end 5a of the post 5. The threaded portion 6 serves for cooperating with a fixation nut described below. Between a threaded portion 6 and the attachment portion 4, a substantially cylindrical section 7 is provided that serves for pivotably coupling the first and second retractor blades 10, 10' to the first and second arms 30, 30', respectively. The cylinder axis C of the cylindrical section 7 extends perpendicular to the thread axis T of the threaded portion 6.

The cylindrical section 7 is oriented relative to the blade portion 2 in such a manner that a transverse axis t going through the center of the cylindrical section 7 and being perpendicular to the cylinder axis C extends substantially perpendicularly to the long side of the blade portion 1. A spring element or portion, such as a leaf spring 8, may be mounted to the rear side 2 of the blade portion 1 close to the lower end 1b. The spring portion 8 may be arranged substantially at the center of the short side of the elongate blade portion 1. In greater detail, the spring portion 8 includes an upper first end 8a and a lower second end 8b, and is curved between the upper end 8a and the lower end 8b. With the upper end 8a, the spring portion 8 may be attached to the blade portion 2, for example, with a screw 9 engaging a threaded hole 11 in the rear side 2. The lower end 8b of the spring portion 8 is free and extends beyond the lower end 1b of the blade portion 1 and away from the rear side. The threaded hole 11 may be provided in an elongate recess 12 that accommodates and guides an upper portion of the spring portion 8.

An end portion 13 of the retractor blades 10, 10' serves to connect the retractor blades 10, 10' to the heads 102 of the bone anchoring elements 100, 100', respectively. The end portion 13 is configured to accommodate at least a portion of the head 102 of the bone anchoring element 100, 100'. As can be seen in greater detail in FIGS. 7 to 10, the end portion 13 includes an upper face 13a and a lower end 13b, and a substantially sleeve-shaped portion 14 adjacent to the lower end 13b. The sleeve-shaped portion 14 includes a first section 14a and a second section 14b. The second section 14b includes a surface that forms a seat 15 for pivotably holding the head 102. As shown in particular in FIG. 10, the surface forming the seat 15 may be spherical-segment-shaped, tapering towards the lower end 13b, so that when the head 102 is inserted, it is prevented from being removed from the second section 14b through the lower end 13b. The surface forming the seat 15 may have any other shape that allows pivoting of the head 102, for example a conical shape. A middle axis or seat axis I of the seat may be substantially parallel to the thread axis T when the end portion 13 is mounted to the blade portion 1. The first section 14a is arranged laterally from the second section 14b in relation to the seat axis I. A lower opening 16 includes a first portion 16a associated with the first section 14a and a second portion 16b associated with the second section 14b. A minimum inner width da at the first portion 16a of the opening 16 is greater than a maximum outer width E of the head 102. A minimum inner width db at the second portion 16b of the opening 16, which can form a bottom of the seat 15, is smaller than the maximum outer width E of the head 102. This allows insertion and removal of the head 102 through the first portion 16a of the opening 16 into and out of the first section 14a, and prevents removal of the head 102 from the second section 14b through the second portion 16b of the opening 16. When seen from the lower end 13b, the portions 16a and 16b of the opening 16 each forms a segment of a circle, wherein the radius of the first portion 16a is greater than the radius of the second portion 16b.

Figure 15A:
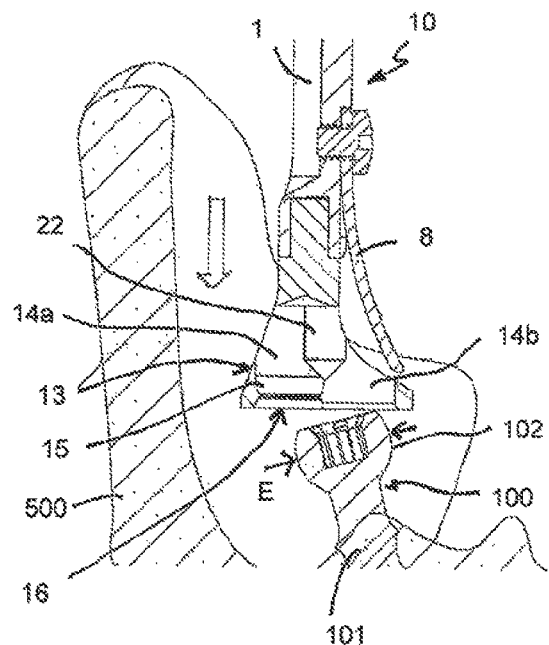
FIGS. 15a to 15d show cross-sectional views of steps of attaching the end portion of a retractor blade of the instrument of FIGS. 1 and 2 to a bone anchoring element, in particular to a pedicle screw, that has been inserted into a pedicle.

The first section 14a and the second section 14b may each have conically widening portions 17a, 17b, respectively adjacent to the lower end 13b for facilitating insertion and pivoting of the bone anchoring element 100, 100'. Adjacent to the upper face 13a, there is an attachment portion 18 that may have a shape that is adapted to a lower end 1b of the blade portion 1. It shall be noted that the blade portion 1 may be thickened adjacent to its lower end 1b to a shape that substantially corresponds to the shape of the attachment portion 18. In greater detail, the attachment portion 18 may have a substantially rectangular contour 18b in a first section that is oriented towards the second section 14b, and may have a circular segment-shaped section 18a that is oriented towards the first section 14a. A lower side 18c of the attachment portion 18 that is directed towards the sleeve-shaped portion 14 may be upwardly inclined and widened. In the center of the upper face 13a of the attachment portion 18, a post 19 that may have an oval cross section is provided for connecting the end portion 18 to the lower end 1b of the blade portion, which includes a corresponding oval-shaped hole. The connection may be a press-fit connection. It shall be noted that the end portion 13 does not need to be a separate part, but can be monolithically formed with the blade portion 1. A curved recess 20 is provided in the first section 14a of the sleeve-shaped portion 14, which starts from the attachment portion 18 and extends steeply towards the lower end 13b and continues less steeply until it reaches an outer end of the first section 14a. By means of this recess 20, an inserted head 102 is permitted to extend out of the first section 14a, as can be seen, for example, in FIG. 15c. A second recess 21 may be provided in the second section 14b. Recess 21 is slightly slanted between the attachment portion 18 and the lower end 13b. Recess 21 may allow the head 102 to extend at least partially therethrough when the head 102 pivots in the seat 15. Furthermore, between the first section 14a and the second section 14b at a distance from the lower end 13b, a longitudinally extending recess 22 is provided at the inner wall of the sleeve-shaped section 14 between the first section 14a and the second section 14b that provides space for moving the head 102 of the bone anchoring element 100, 100' from the first section 14a laterally into the second section 14b. The longitudinal recess 22 may end at a distance from the lower end 13b and at a distance from the smallest width of the seat 15. A lower surface of the attachment portion 18 forms an abutment 23 for an inserted head 102, limiting upward movement of the head 102 in the direction of or parallel to the seat axis I. As can be seen in particular in FIG. 1 and FIGS. 6a to 6c, the end portion 13 is connected to the blade portion 1 in such an orientation that the first section 14a is facing towards the spring portion 8. In the mounted state, the spring portion 8 extends into the first recess 20. Preferably, the spring portion 8 extends to a distance from an upper edge 24 of the first section 14a, as shown in FIG. 15a, for example.

Turning now to FIGS. 6a to 6c, a plurality of retractor blades 10 may be provided that can be used interchangeably with the instrument and that differ in terms of the length of their respective blade portions 1, 1', 1".

Referring in particular to FIGS. 1 and 2, the attachment of the first and second retractor blades 10, 10' to the arms 30, 30' will be explained. The second mounting portion 32 of the first arm 30 includes an elongate through hole 33, an inner contour of which corresponds substantially to the outer contour of the cylindrical section 7 of the retractor blade 10 in such a manner that the cylindrical section 7 can be guided into the through hole 33 and accommodated therein. As the through hole 33 is elongate, pivoting of the cylindrical section 7 in the through hole 33 is limited to pivoting in a single plane that is defined by the thread axis T and the transverse axis t shown in FIG. 5. The orientation of the long sides of the elongate through hole 33 with respect to the longitudinal axis a of the first arm 30 when the first arm 30 is in a straight configuration is in the example shown about 45° inclined towards the second arm 30'. Hence, as the blade portion 1 extends with its rear side 2 and the front side 3 perpendicular to the cylindrical section 7 and the transverse axis t, the blade portion 1 of the first retractor blade is oriented at an angle of approximately 45° outward and away from the second arm 30'.

The second mounting portion 32 of the second arm 30' includes in a similar manner an elongate through hole 33', the orientation of which is, however, mirror symmetrical to the orientation of the elongate through hole 33, so that the planes extending through the centers and parallel to the long sides of the elongate through holes 33, 33' form a predefined angle, for example an angle of approximately 90°, preferably 90°. As a result thereof, when the second retractor blade 10' is mounted with its cylindrical section 7 in the through hole 33' of the second arm 30, the blade portions 1 of the first retractor blade 10 and the second retractor blade 10' from a predefined angle α, for example, an angle of approximately 90°, which is open towards the positioning rod 50 as depicted in FIG. 1. It shall be noted that the orientation of the through holes may be such that an angle greater or smaller than 90° between the blade portions 1 of the first retractor blade 10 and the second retractor blade 10' may be achieved.

Figure 16:
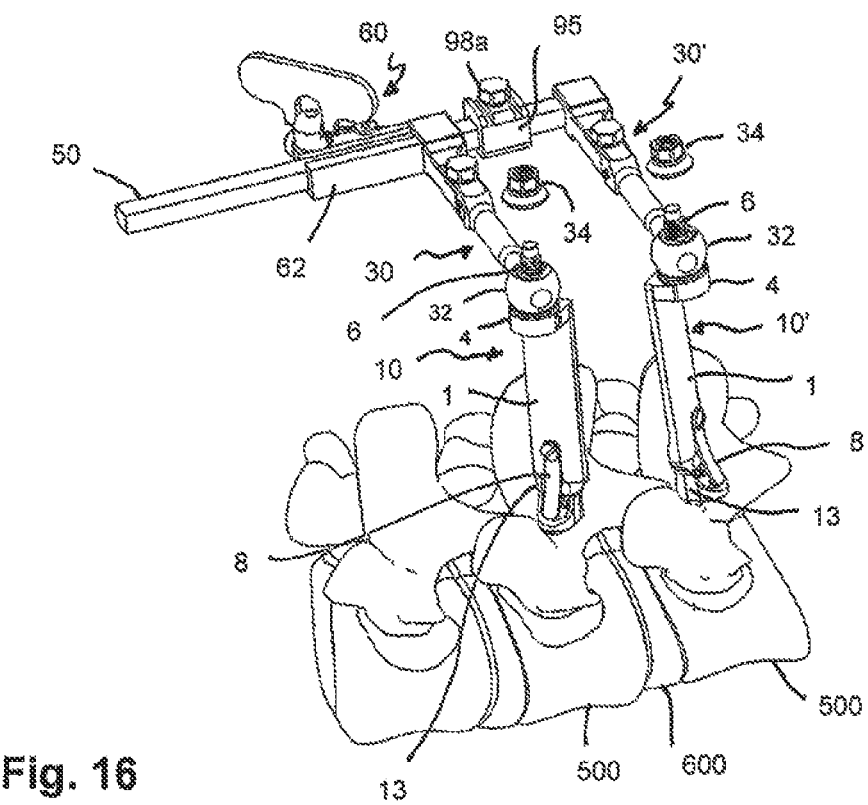
FIG. 16 shows a perspective of a step of attaching the arms and the frame to the retractor blades of the instrument of FIGS. 1 and 2.

The length of each through hole 33, 33' from an upper side of the second mounting portion 32 to a lower side may be such that the threaded portion 6 of the post 5 extends out of the mounting portion 32, as depicted in FIG. 16. An outer surface of the mounting portion 32 may be spherically shaped. An upper surface 4a of the attachment portion 4 around the post 5 may have a corresponding spherical shape to form an abutment for the second mounting portion 32.

Figure 11:
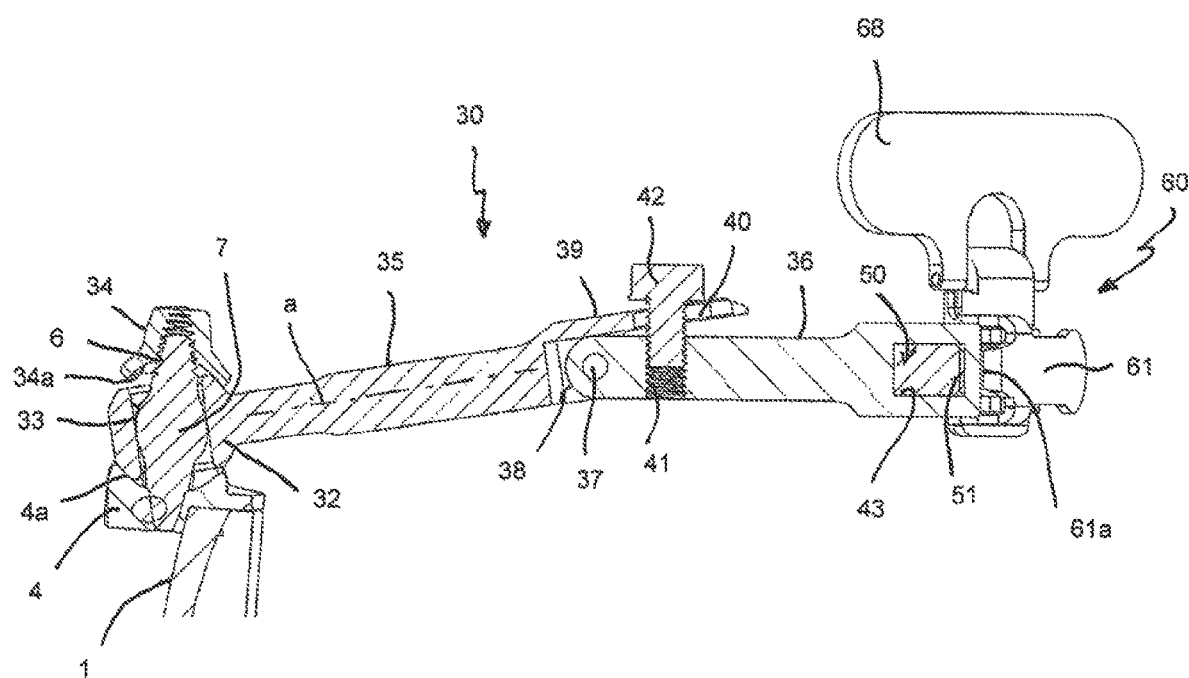
FIG. 11 shows a cross-sectional view of an arm of the instrument of FIGS. 1 and 2.

To fix the first and second retractor blades 10, 10', a nut 34 is provided that can be screwed onto the threaded portion 6 of the post 5 to press the mounting portion 32 against the attachment portion 4, thereby locking the cylindrical section 7 in the through hole 33, 33' (see also FIG. 11). As can be seen in greater detail in FIG. 11, the nut 34 may be a cover nut that may have a spherical underside 34a that slides on the spherical outer surface of the mounting portion 32. By means of the cooperating spherical surfaces, the retractor blades 10, 10' can be fixed at a particular pivot angle with respect to the arms 30, 30', respectively.

Next, referring also to FIGS. 1, 2 and 11, the arms 30, 30' and their attachment to the positioning rod 50 will be explained in greater detail. Each of the first and second arms 30, 30' includes a first arm portion 35 adjacent to the second mounting portion 32 and a second arm portion 36 adjacent to the first mounting portion 31 that is attached to the positioning rod 50. The first arm portion 35 and the second arm portion 36 are connected to each other via a hinge 37, for example, a screw extending through an eyelets as shown in FIGS. 2 and 11, that provides a pivot axis perpendicular to the arm axis a defined by the first arm portion 35. The first arm portion 35 has at a side opposite to the second mounting portion 32 a recess 38 for the hinge parts and an extension portion 39 that extends over the second arm portion 36 and that covers the free end and the hinge parts of the second arm portion 36. At a distance from its free end, the extension portion 39 includes a through hole 40, and the second arm portion 36 includes a threaded hole 41 at a corresponding position, so that a connection screw 42 can extend through the through hole 40 and can be threaded into the threaded hole 41 to limit a pivoting motion of the second arm portion 36 relative to the first arm portion 35 around the hinge 37. When the first and second arms 30, 30' are in a straight configuration, i.e., where the first and second arm portions 35, 36 are substantially aligned, the extension portion 39 abuts along its length against an upper surface of the second arm portion 36. This straight configuration can be fixed by screwing the connection screw 42 fully into the threaded hole 41 until it abuts against an upper side of the extension portion 39. In an angled configuration, the connection screw 42 is only partially screwed into the threaded hole 41 so that there is play to allow for a pivoting motion of the second arm portion 36 relative to the first arm portion 35. The second arm portion 36 can be pivoted downward. Preferably, the angled configuration is not fixable. Thereby, it is possible, that an optimum angle can be achieved. This means that during surgery, the positioning rod 50 and the second arm portions 36 can be positioned closer to a patient's body surface.

The first mounting portion 31 of the first arm 30 includes a passage 43 that extends substantially perpendicularly to the arm axis a when the arm 30 is in a straight configuration. The passage 43 is configured to slidably receive the positioning rod 50 therein. Preferably, the passage 43 has a cross section, for example, a rectangular cross section, that allows receipt of the positioning rod in a form-fit manner to prevent rotation of the arm 30 around the positioning rod 50.

The positioning rod 50 may have a substantially rectangular cross section. On the surface of the short side of the rectangle that is facing away from the first arm portion 35, a ratchet structure 51 is provided on the positioning rod 50 (shown in FIG. 4 and FIG. 11) that permits an incremental movement of the first arm 30 relative to the second arm 30' using the displacement mechanism 60. The ratchet structure 51 may include, for example, triangular or rounded teeth or any other structure that permits incremental movement along the rod axis.

As depicted in particular in FIGS. 1 to 4 and 11, the displacement mechanism 60 includes an engagement member 61. The engagement member 61 has a hook-like front portion 61a that is configured to engage the ratchet structure 51. Furthermore, the engagement member 61 is hingedly attached to a holding frame 62, which is connected to the first mounting portion 31 of the first arm 30 and therefore, can slide with the first mounting portion 31 along the positioning rod 50. A spring 63 is provided to urge the engagement member 61 with the engagement portion 61a into the valleys of the ratchet structure 51. By means of this, in the resting position of the engagement member 61, the hook-like portion 61a engages the ratchet structure 51. A rear portion 61b of the engagement member 61 opposite to the engagement portion 61a is configured to be pushed against the spring force, so that the engagement member 61 pivots around the pivot axis 64 that extends through lateral eyelets 65 of the engagement member 61. Consequently, pushing the engagement member 61 against the spring force of the spring 63 moves the hook-like front portion 61a out of engagement with the ratchet structure 51 and permits sliding movement of the first arm 30 along the axis of the positioning rod 50.

The sliding movement of the first arm 30 along the positioning rod 50 can be effected in two ways. In a first way, the rear portion 61b of the engagement member 61 is pushed against the spring force by hand through a user. The front portion 61a is consequently out of engagement with the ratchet structure 51 as long as the rear portion 61b is pushed. This allows continuous sliding movement of the first arm 30. In a second way, an incremental movement in steps corresponding to the distance of the peaks or valleys of the ratchet structure 51 is enabled. To achieve this, a rotary mechanism 66 is provided that includes, for example, a gear or other circumferential ratchet structure 67 that cooperates with the ratchet structure 51 on the positioning rod 50. The gear 67 is operatively connected to the engagement member 61 and urges the spring 63 back every incremental rotational step. By means of this, the engagement member 61a is released from engagement with the ratchet structure 51 every rotational step. A handle 68 may be provided for effecting the rotation. By rotating the incremental rotation mechanism 66, precise incremental or stepwise movement of the first arm 30 relative to the second arm 30' can be achieved.

Figure 12:
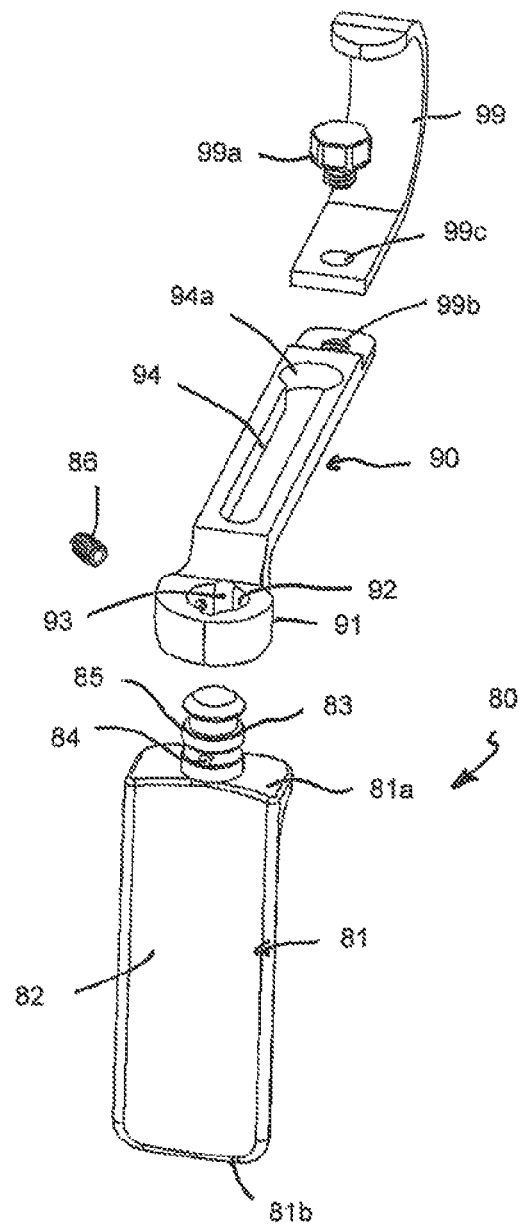
FIG. 12 shows a perspective exploded view of a third retractor blade of the instrument of FIGS. 1 and 2.

Referring now additionally to FIG. 12, the third retractor blade 80 will described. Third retractor blade 80 includes a blade portion 81 with a front side 82 that faces the front sides 3 of the blade portions 1 of the first retractor blade 10 and the second retractor blade 10' in a mounted state on the positioning rod 50. The front face 82 may be concave. The blade portion 81 is elongate and may have a substantially rectangular contour. At a first end 81a that is opposite to a lower free end 81b, a mounting post 83 is provided at approximately a center of a surface of the upper end 81a. The mounting post 83 is configured to be received in a mounting portion of a third arm 90, as explained below. For preventing rotation, a transverse pin 84 that is to be received in a groove is provided. The mounting post 83 may have a ring shaped projection 85 that may be received in the mounting portion of the third arm 90 and secured there, for example, by a set screw 86.

The third arm 90 includes at one end a mounting portion 91 that has through hole 92 for receiving the post 83 of the third blade 80. A groove 93 extends in a direction parallel to the center axis of the mounting post 83 to receive the transverse pin 84. By means of this, the blade portion 81 can be mounted to the third arm 90 in a correct orientation. The third arm 90 further includes an elongate hole 94 that serves for positioning the blade portion 81 relative to the positioning rod 50 at a variable distance in a direction perpendicular to the rod axis. The third arm 90 further includes a second mounting portion 95, as shown in greater detail in FIG. 2, that includes a through hole 96 to slidably receive therein the positioning rod 50. In a top surface 95a of the second mounting portion 95, a threaded hole 97 is provided that receives a clamping screw 98, a head 98a of which has a greater outer width than the transverse width of the elongate through hole 94. An end portion 94a of the elongate through hole is broadened so as to permit passing through of the head 98a of the clamping screw 98. Moreover, the third arm 90 is guided relative to the second mounting portion 95, for example, via guide grooves 97a. When the second mounting portion 95 is mounted to the positioning rod 50 between the first and second arms 30, 30', the pre-assembled third arm 90 with the mounted retractor blade 80 can be attached to the second mounting portion 95 by guiding the head 98a of the clamping screw 98 through the enlarged portion 94a of the elongate hole 94. Then, the third arm 90 with the blade portion 81 attached thereto can slide with the elongate recess 94 along the clamping screw 98, in particular, the third arm 90 and the blade portion 81 can be pulled backward, away from the first and second retractor blades 10, 10', until the blade portion 81 is at a suitable distance from the positioning rod 50. This position can be fixed by tightening the clamping screw 98. To slide the third arm 90 along the clamping screw 98, a handle, for example, in the form of an upwardly bent hook 99, may be provided that is attachable to the third arm 90 via a clamping screw 99a that engages a threaded hole 99b and extends through a through hole 99c of the hook portion.

The blade portion 81 may optionally have a rearward extension (not shown) at the lower end 81b that extends away from the blade portions 1 of the first and second retractor blades 10, 10' and that may have a hook-like function for engaging and retracting soft tissue. The connection between the retractor blade 80 and the mounting portion 91 allows to quickly and safely attach and detach various blade portions that may differ in size, in particular, in length or other characteristics.

The parts and portions of the instrument may be made of any material, preferably, however of titanium or stainless steel or any body-compatible metal alloy or plastic material. In particular the blade portions 1 and the end portions, as well as the blade portion 81, should be made of body compatible material, such as titanium or other body compatible metals or metal alloys or of body compatible plastics, such as polyether ether ketone (PEEK).

Figure 13:
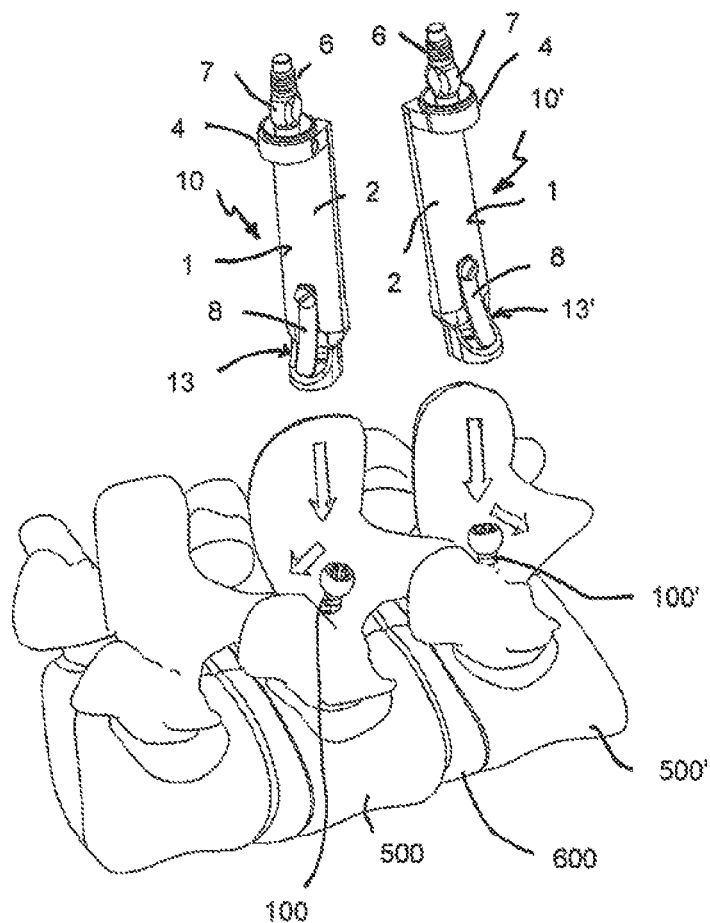
FIGS. 13 and 14 show steps of attaching the retractor blades of the instrument of FIGS. 1 and 2 to pedicle screws inserted into the pedicles of adjacent vertebrae.
Figure 14:
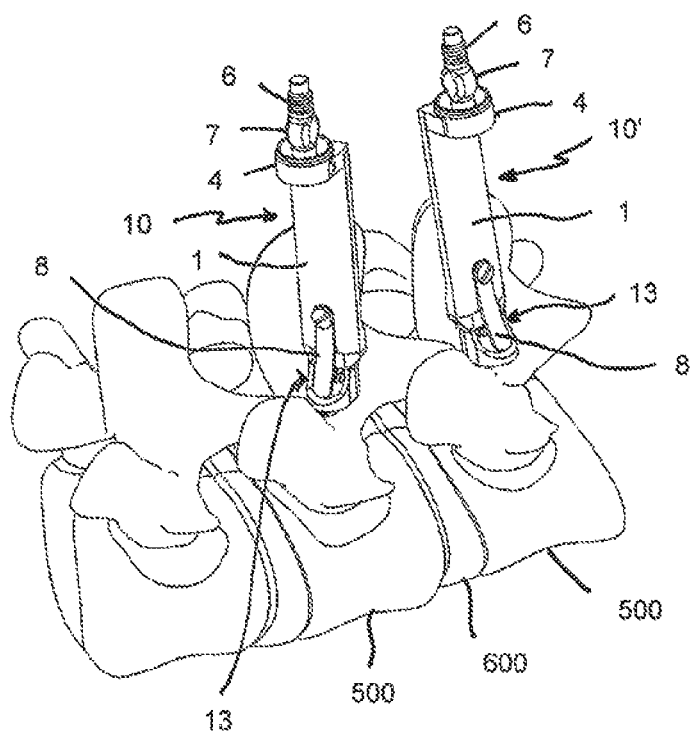
Figure 15B:
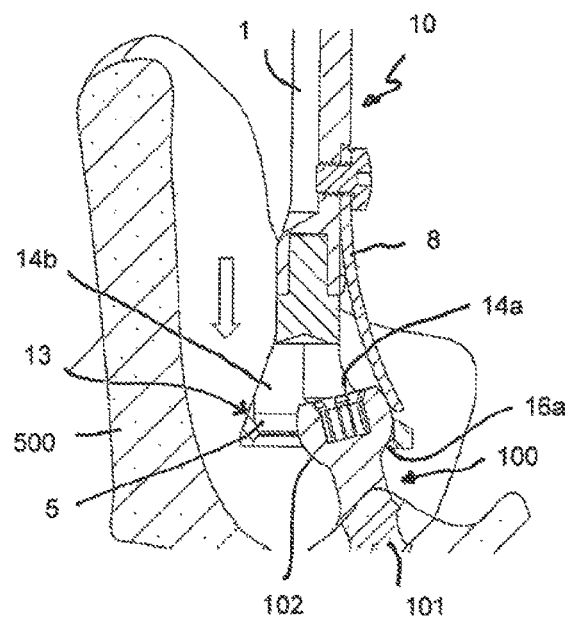
Figure 15C:
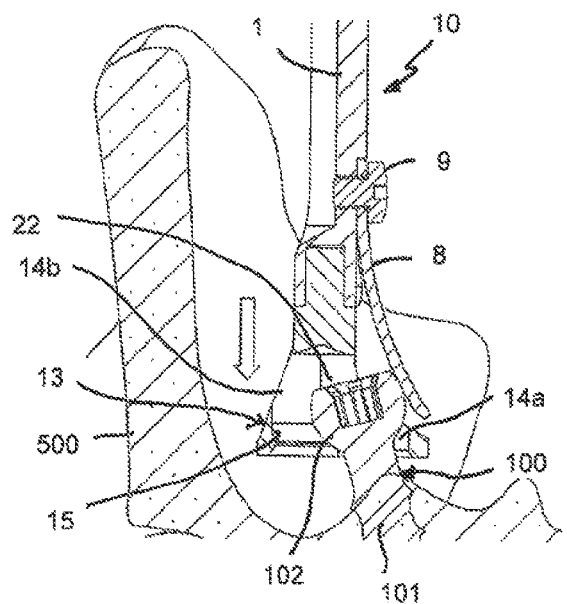
Figure 15D:
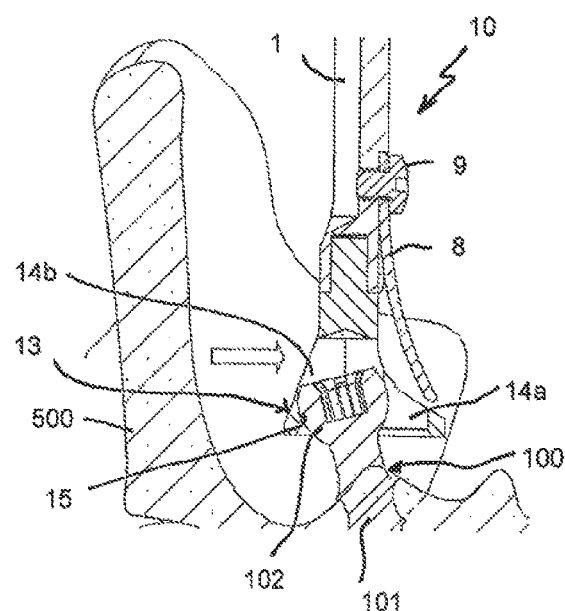

Use of the instrument will be described with reference to FIGS. 13 to 19. In FIGS. 13 and 14, the pedicle screws 100, 100' have been inserted into the pedicles of adjacent vertebrae 500, 500'. In an example of application, the intervertebral disk 600 is to be removed and replaced by a cage in order to stabilize the spinal motion segment associated with the vertebrae 500, 500'. As illustrated in FIGS. 13 and 14, the first retractor blade 10 and the second retractor blade 10' are placed onto the heads 102 of the bone anchoring elements 100, 100', respectively. In greater detail, as shown in FIG. 15a, during placement of the first or second retractor blade onto the head, the head enters the first section 14a of the end portion 13 through the first opening section 16a and abuts against the inner side of the spring portion 8 (FIG. 15b). During further insertion, as shown in FIG. 15c, an increasing force is exerted by the spring portion 8 onto the head 102 that contributes to urging the head 102 into the second section 14b of the end portion, or, in other words, to moving the end portion 13 laterally relative to the head 102 so that the head comes into the second section 14b. Due to the shape of the recess 22, the head 102 easily moves into the seat 15 with the aid of the spring portion 8. As shown in FIG. 15d when the head 102 has entered the seat 15, the retractor blade 10 is moved outwards relative to the head to fix the retractor blade to the bone. The first and second retractor blades 10, 10' are still rotatable and pivotable around the head 102 as the seat 15 provides a polyaxial connection.

Figure 17:
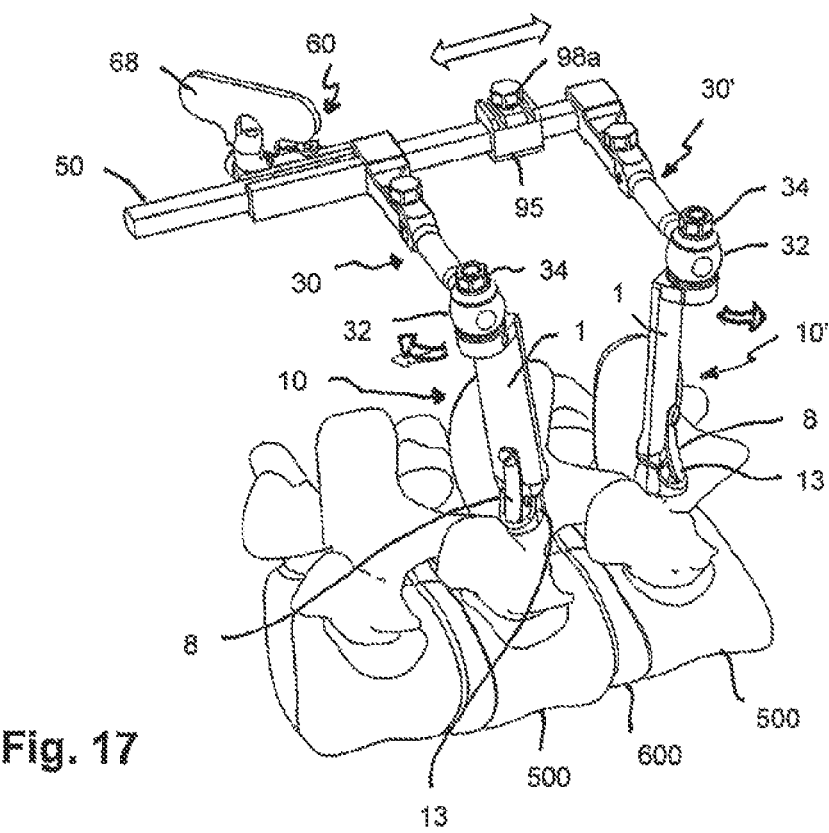
FIG. 17 shows a perspective view of a step of only retracting tissue with the instrument of FIGS. 1 and 2.

Next, as shown in FIG. 16, the positioning rod 50, with the first and the second arms 30, 30' mounted thereon and optionally the first mounting portion 95 of the third retractor blade 80 mounted between the first and second arms 30, 30', is attached to the retractor blades 10, 10'. The first and second retractor blades 10, 10' are oriented such that their cylindrical sections 7 can be inserted into the through holes 33, 33'. As the orientation of the through holes 33, 33' with respect to each other is fixed and corresponds to a predefined angle, for example, approximately or exactly 90°, the blade portions 1 of the first and second retractor blades 10, 10' will also form a corresponding predefined angle, correspondingly 90° for example, with respect to each other. As shown in FIG. 17, the nuts 34 are screwed onto the threaded portions 6 of posts 5 but not yet tightened. Consequently, as shown by the arrows in FIG. 17, due to the cylindrical sections 7 received in the through holes 33, 33', the first and second retractor blades 10, 10' are pivotable in a single plane. When the distance of the arms 30, 30' relative to each other is increased or decreased by actuating the displacement mechanism 60, the first and second retractor blades 10, 10' can pivot in that single plane and the blade portions 1 can pivot outwards in their V-orientation relative to each other, as indicated by the curved arrows. On the other hand, the retractor blades 10, 10' are also pivotable relative to the heads 102. Thereby, forces acting onto the bone are minimized or reduced. In FIG. 17, the first and second retractor blades 10, 10' are used for retraction of tissue.

Figure 18:
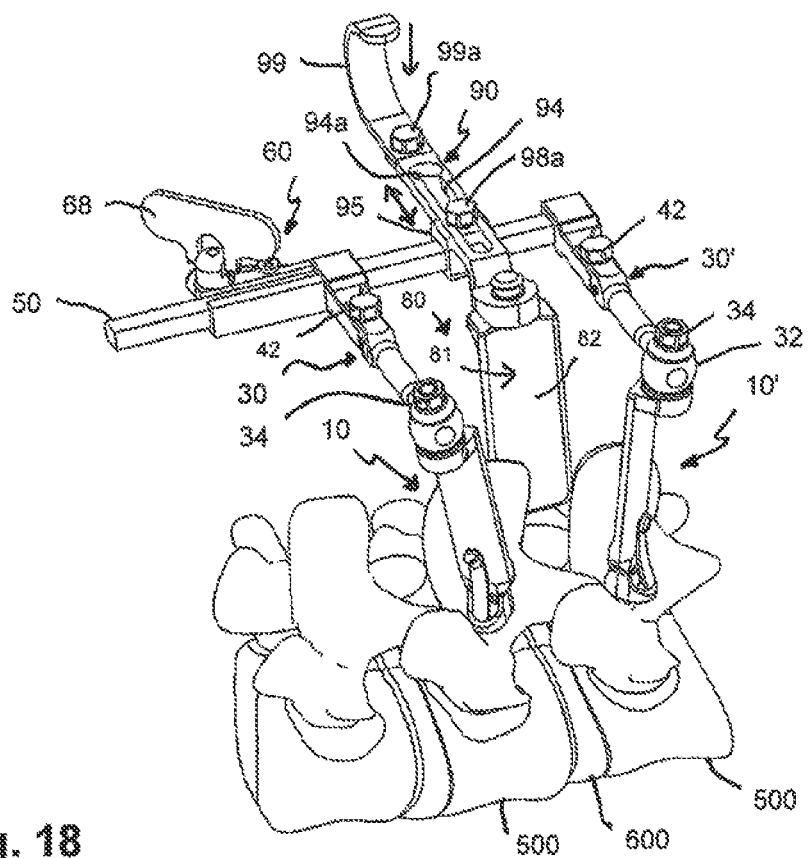
FIG. 18 shows a step of attaching the third retractor blade of the instrument of FIGS. 1 and 2 to the frame between the arms, and retracting tissue to allow for better access to the intervertebral space.

Next, as depicted in FIG. 18, the third retractor blade 80, which has been mounted to the arm 90 in an orientation such that its front surface 82 faces towards the blade portions 1 of the first and second retractor blades 10, 10', is placed on the mounting portion 95 to attach the third retractor blade 80 to the positioning rod 50. The head 98a of the clamping screw 98 is guided through the enlarged end 94a of the elongate through hole 94 and moved laterally relative to the elongate through hole 94 so that the arm cannot be removed. Then, with the handle 99 the third retractor blade 80 is drawn backwards, thereby retracting soft tissue from the surgical site. Once, the opening created by the first and second retractor blades 10, 10' and the third retractor blade 80 is large enough to provide access to the intervertebral disc 600, the position of the third retractor blade 80 is fixed by tightening the clamping screw 98.

Figure 19:
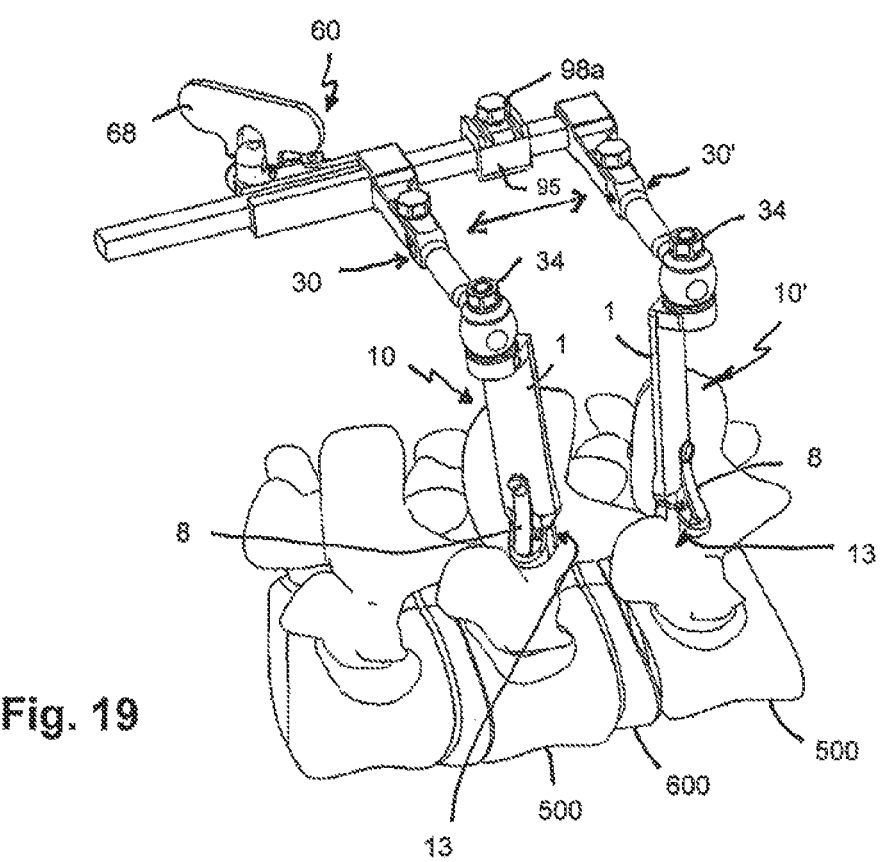
FIG. 19 shows a step of distracting adjacent vertebrae while the retractor blades of the instrument of FIGS. 1 and 2 are fixedly connected to the arms.

Finally, as shown in FIG. 19, the nuts 34 are tightened to lock the angular position of the first and second retractor blades 10, 10'. Once the angular position of the first and second retractor blades 10, 10' is locked, the arm 30 can be displaced relative to the arm 30' with the displacement mechanism 60 to perform distraction on the vertebrae 500, 500'. Still, the retractor blades 10, 10' can be pivotable relative to the heads 102. Thereby, forces acting onto the bone can be reduced. In FIG. 19 the third retractor blade 80 has been removed again. Alternatively, the third retractor blade can stay on the positioning rod 50. When the distance between the first and second arms 30, 30' is increased, the intervertebral space between the vertebrae 500, 500' may be enlarged. Thereby, it is possible to remove the intervertebral disk and to insert a cage.

After use of the instrument on one side, the first and second retractor blades 10, 10' are removed. Thereafter polyaxial receiving parts may be placed onto the heads 102 of the pedicle screws and a spinal fixation rod may be inserted into the receiving parts and fixed thereto.

In the above illustrations, the first and second arms 30, 30' are in the straight configuration. If the situation at the surgical site requires it, the connection screws 42 may be loosened to permit the second arm portions 36, together with the positioning rod 50, to assume an angled configuration relative to the first arm portions 35, as shown, for example, in FIG. 11.

Another embodiment of the instrument will be explained, referring to FIGS. 20 to 25c. The instrument of FIGS. 20 to 25c differs from the instrument of the embodiment described before in the construction and functionality of the arms. All other parts are identical or very similar to those of the previously described embodiments. Identical or very similar parts and portions are marked with the same reference numerals, and the descriptions thereof will not be repeated.

The instrument includes a first arm 300 and a second arm 300'. The first arm 300 is associated with the first mounting portion 31 that is connected to the holding frame 62' of the displacement mechanism 60. It shall be noted that the holding frame 62' is very similar to the holding frame 62 of the previous embodiments, but holds the displacement mechanism along opposite sides of the positioning member 50 that are adjacent to and on either side of the ratchet structure 51. The second arm 300' is associated with the first mounting portion 31 that is fixedly connected to the positioning member 50 at an end of the positioning member.

Each of the first and second arms 300, 300' includes a first arm portion 350 adjacent to the second mounting portion 320 which receives the blades 10, 10' and a second arm portion 360 adjacent to the first mounting portion 31 that is attached to the positioning rod 50. The first arm portion 350 and the second arm portion 360 are connected to each other via a connection structure 400. The connection structure 400 is configured to permit a pivoting or rotation of the first arm portion 350 relative to the second arm portion 360. Thereby, as indicated by the arrows in FIG. 21 and FIGS. 25a to 25c, additional degrees of freedom for positioning of the first and second retractor blades 10, 10' can be realized. In particular, by means of this design, the connection between the first and second retractor blades, for example, does not need to be pivotable.

The second mounting portion 320 includes a through-hole 330 that extends perpendicular to a longitudinal extension of the first arm portion 350, and serves for receiving respective portions of the retractor blades 10, 10' as in the previous embodiments. In one embodiment (not shown), for example, the retractor blades 10, 10' can be clicked into the second mounting portions 320, respectively, and held therein in a single angular position.

Figure 20:
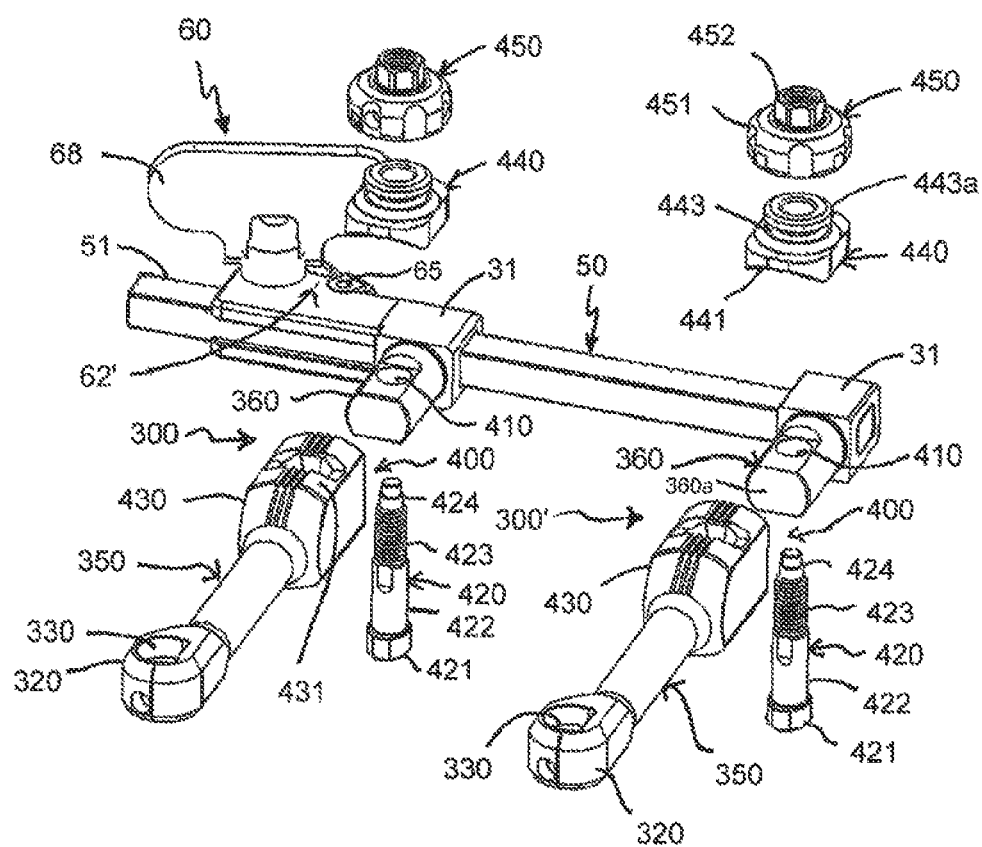
FIG. 20 shows a perspective exploded view of another embodiment of the instrument.
Figure 21:
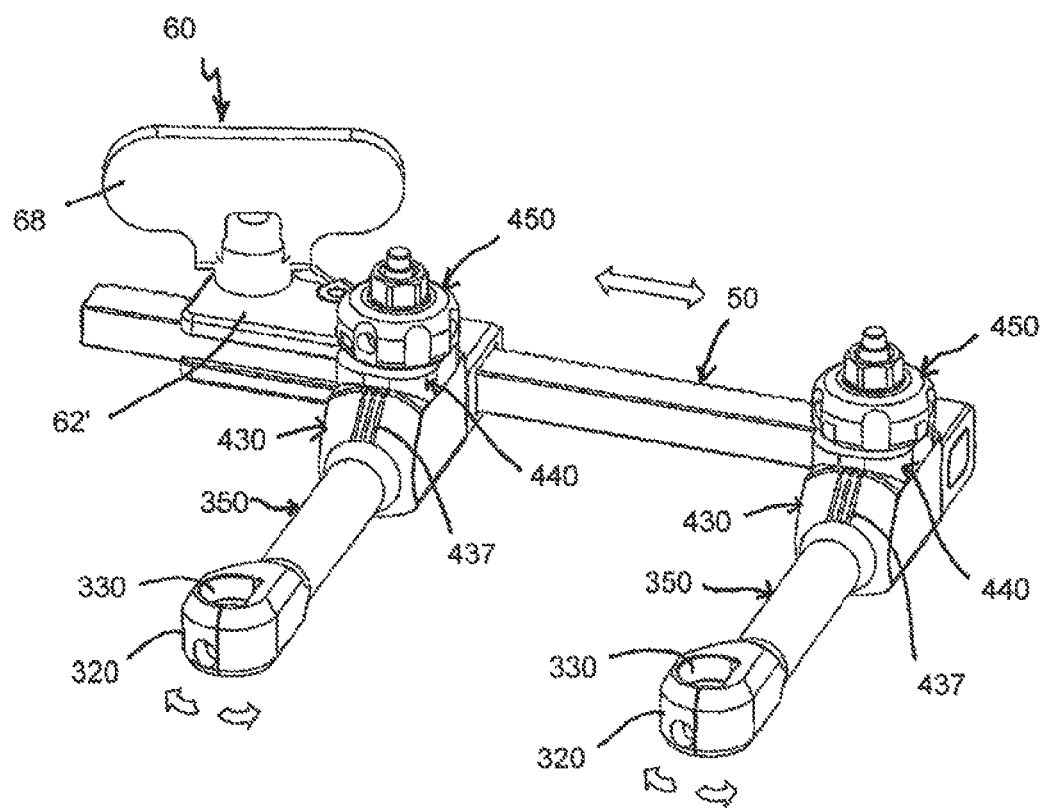
FIG. 21 shows a perspective view of the instrument of FIG. 20 in an assembled state.
Figure 22:
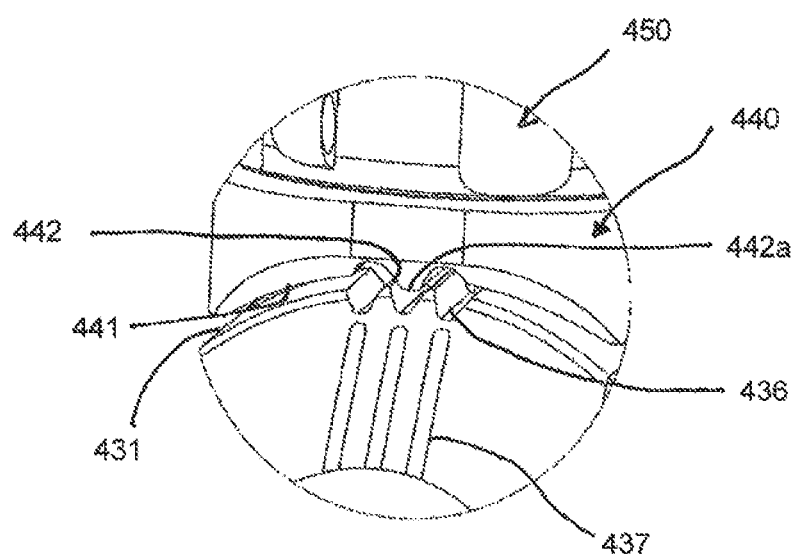
FIG. 22 shows a detail of FIG. 21.
Figure 23:
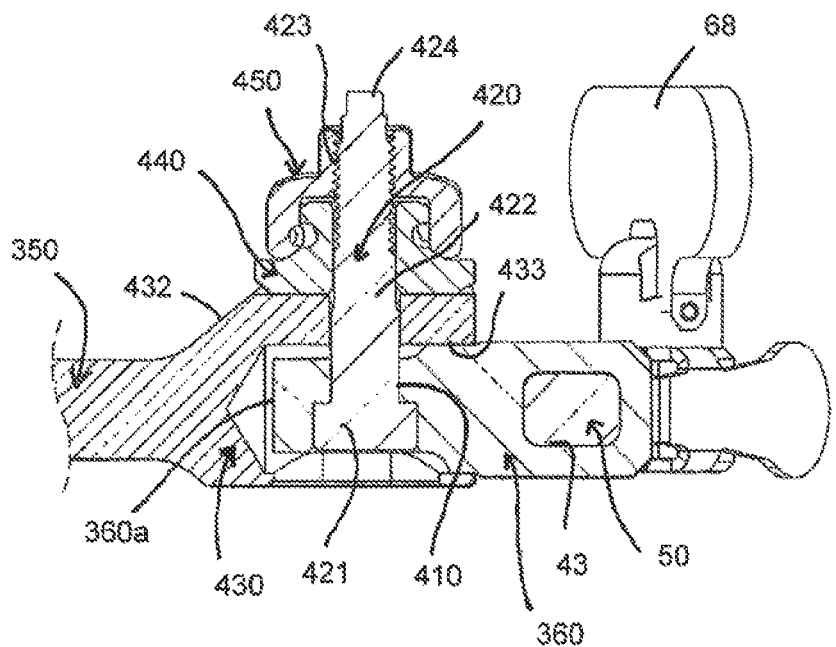
FIG. 23 shows a cross-sectional view of a portion of the instrument of FIGS. 20 and 21, the cross-section taken in a plane that is perpendicular to a lengthwise extension of a positioning member and that extends through a lengthwise extension of the first arm.

As depicted in FIGS. 20 and 23, the second arm portion 360 includes a passage 410 that is configured to receive a connection pin 420 therethrough. The cross-section of the second arm portion 360 is, in a region adjacent the free end 360a, substantially elongate with opposite circular short edges, obtained, for example, by cutting opposite and parallel flat faces into a cylindrical projection.

Figure 24:
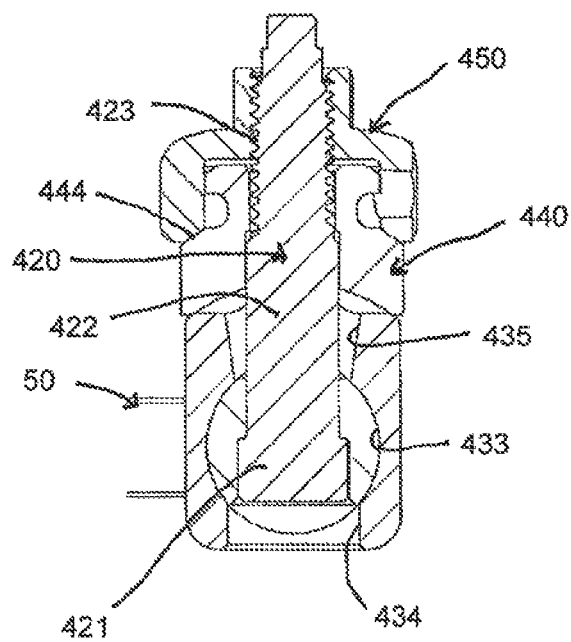
FIG. 24 shows a cross-sectional view of a portion of the instrument of FIGS. 20 and 21, the cross-section taken in a plane that is parallel to the lengthwise extension of the positioning member, that is perpendicular to the lengthwise extension of the first arm, and that extends through a center of a connection between a first arm portion and a second arm portion of the first arm.

The connection pin 420 includes a head portion 421 and, adjacent thereto, an unthreaded portion 422 with a reduced width, followed by a threaded portion 423 and a tip portion 424. Hence, the passage 410 is adapted to receive the head portion 421 and a part of the unthreaded portion 422 of the connection pin 420. As shown in FIGS. 23 and 24, which depict views of the cross-section of the connection pin that are rotated by 90° from one another, the head 421 of the connection pin 420 is mirror-symmetrical and not rotatable in the passage 410. Thereby, the connection between the second arm portion 360 and the pin 420 is a form-fit connection.

Figures 25A, 25B, 25C:
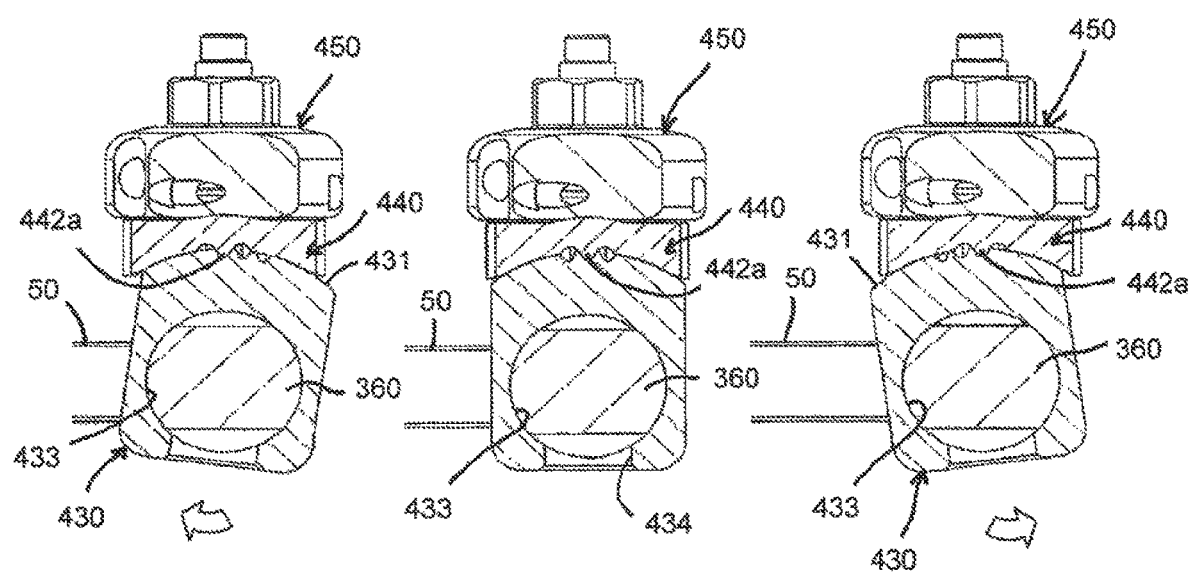
FIGS. 25a to 25c show different cross-sectional views of the connection between the first arm portion and the second arm portion, in three different pivot positions of the first arm portion relative to the second arm portion, wherein the cross-section is taken in a plane parallel to the positioning member and further away from the positioning member towards a second mounting portion, compared to the cross-section of FIG. 24.

The connection structure 400 further includes a connection body 430 that has a substantially cylindrical upper side 431, with the cylinder axis being perpendicular to the longitudinal axis of the positioning member 50. Otherwise, the connection body 430 may be substantially cuboid-shaped and may have a slanted front face 432 that faces towards the second mounting portion 320. The connection body 430 includes a cylindrical bore 433 that is open towards the second arm portion 360 and closed at its opposite end, and that serves for receiving the second arm portion 360 partially therein. As best seen in FIGS. 25a to 25c, the cylindrical bore 433 has a size such that the connection body 430 can pivot relative to the second arm portion 360. In the assembled state, the passage 410 is located in the bore 433. To permit the connection pin 420 to be inserted, the connection body 430 includes a bottom transverse through-bore 434 that extends from a side of the connection body opposite the cylindrical surface 431 into the bore 433. Opposite to the through-bore 434, an opening 435 is formed in the connection body 430 that permits the connection pin 420 to extend therethrough and protrude out of the cylindrical upper surface 431. The opening 435 is mirror-symmetrical but not rotationally symmetrical. In the direction perpendicular to the longitudinal axis of the positioning member 50, as shown in FIG. 23, the opening 435 holds the connection pin 420 so that it cannot pivot relative to the connection body 430 about an axis that is parallel to the longitudinal axis of the positioning member 50. In the 90° rotated direction as depicted in FIG. 24, the opening 435 is conically widening towards the cylindrical upper surface 431, so that the connection body 430 can pivot relative to the second arm portion 360 about an axis that is perpendicular to the longitudinal axis of the positioning member 50. Since the connection body 430 is a part of the first arm portion 350, the first arm portion 350 can also pivot relative to the second arm portion 360 about the same axis.

The connection pin 420 has a length such that the unthreaded portion 422 protrudes out of the cylindrical surface 431 when the connection pin 420 is received.

The connection body 430 further includes an engagement structure in the form of a groove structure 436 including a plurality of, in the embodiment shown three, substantially parallel grooves that extend in the lengthwise direction of the first arm portion 350, formed in the cylindrical surface 431. Corresponding parallel indication grooves 437 may be provided in the inclined surface 432 which may assist a user in adjusting the first arm portions 350 to a desired pivot position.

The connection structure 400 further includes an adjustment member 440 and a fixation member 450. A corresponding engagement structure at the adjustment member 440 provides an engagement between the connection body 430 and the adjustment member 440 configured to permit adjustment to various engagement positions. As can be seen in particular in FIGS. 20, 21 and 22, the adjustment member 440 includes a cylindrical lower surface 441 matching the cylindrical surface 431 of the connection body 430, with an engagement structure in the form of a projection or rib and groove structure 442 extending parallel to the cylinder axis and having a central projection 442a. The projection and groove structure 442 is configured to cooperate with the groove structure 436 to adjust a pivot position of the connection body 430 relative to the second arm portion 360. With three grooves of the groove structure 436, the central projection 442a can assume three positions. A zero position is defined when the central projection 442a engages the central groove (FIG. 25b). In the zero position, the first arm portion 350 and the second arm portion 360 are aligned in such a manner that the central bore 330 of the second mounting portion 320 is perpendicular to the longitudinal axis of the positioning member 50. Second and third pivot positions (FIGS. 25a and 25c) are defined by the central projection 442a engaging the grooves to the right and to the left of the central groove, respectively, of the groove structure, so that the first arm portion 350 is pivoted in one direction or the other direction, respectively. In the embodiment shown, the pivot angle may be around ±5°. Hence, the bore axis of the retractor blade receiving bore 330 of the second mounting portion 320 is also pivoted.

The adjustment member 440 further includes, opposite to the cylindrical surface 441, a substantially tubular connection portion 443 with a collar 443a, wherein the tubular connection portion 443 is receivable in the fixation member 450 and rotatable relative thereto. The fixation member 450 is a nut member including a lower part 451 that is configured to cooperate with and press onto an outer slanted surface 444 of the adjustment member 440, and an upper part 452 that is configured to cooperate with the threaded portion 423 of the connection pin 420.

As shown in FIG. 23, when the connection pin 420 extends through a first arm portion 350 and a second arm portion 360 and protrudes out of the connection body 430, the adjustment member 440 engages the cylindrical surface 431, and the fixation member 450 rotatably holds the adjustment member 440 and engages the threaded portion 423 of the connection pin 420. The connection pin 420 preferably has a length such that it may protrude out of the fixation member 450.

In use, when the fixation member 450 is not tightened, the connection body 430 can pivot relative to the adjustment member 440 as depicted in FIGS. 25a and 25c. Thereby, the cylindrical surfaces of the connection body 430 and of the adjustment member 440 slide along each other, until the central projection 442a snaps into one of the grooves of the groove structure 436. The respective pivot position is fixed by tightening the fixation member 450, which presses onto the slanted surface 444 of the adjustment member 440, which in turn firmly engages the central projection 442a with one of the grooves of the groove structure 436. Thereby, the pivot position is fixed.

It shall be noted that the above described embodiments have robust structures and are easy to operate. Various positions of the retractor blades can be adjusted. The engagement structures can also further be designed to provide more refined positions. The retractor blades can be adjusted independently from each other.

Modifications of the above described embodiments are also possible. For example, the shape of the blade portions or of the retractor blades as a whole may be different. Also, the spring force may be generated by a spring other than a leaf spring. The displacement mechanism may be constructed in a different manner. The third retractor blade may be omitted. The frame can be shaped other than in the form of a positioning rod. Any shape that allows a displacement of the first arm 30 relative to the second arm 30' may be conceivable.

The instrument may also be used for performing other surgical steps in the procedure, for example for compressing vertebrae or bone parts towards each other. In this case the retractor blades may be mounted, for example, to the arms in a 180° rotated configuration.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument configured to attach to a bone anchoring element during surgery, the instrument comprising:
    an elongate portion; and
    an end portion having a first side and an opposite second side, wherein the elongate portion extends away from the first side, and wherein an opening is defined at the second side to accommodate at least a portion of a head of the bone anchoring element;
    wherein the opening of the end portion has a first section with a first width that permits insertion and removal of the head through the second side of the end portion, and a second section forming a seat with a width that is smaller than the first width to prevent removal of the head from the second side when the head is held in the seat; and
    wherein a region of the opening between the first section and the second section remains unobstructed by other portions of the instrument to facilitate unhindered movement of the head from the second section towards the first section.

2. The instrument of claim 1, wherein a longitudinal axis extends substantially through a center of the seat, and wherein the first section is arranged laterally to the second section relative to the longitudinal axis, such that the instrument is movable relative to the head in a direction transverse to the longitudinal axis to move the head between the first and second sections of the opening.

3. The instrument of claim 1, further comprising a spring portion configured to urge the head from the first section of the opening towards the second section of the opening.

4. A tool for distraction and/or retraction comprising:
    the instrument of claim 1 forming a first retractor blade;
    a second retractor blade;
    a frame;
    a first arm for coupling the first retractor blade to the frame; and
    a second arm for coupling the second retractor blade to the frame.

5. The tool of claim 4, wherein each of the first and second retractor blades and/or each of the first and second arms comprises a coupling portion respectively configured to couple the first and second retractor blades to the first and second arms, such that blade portions of the first and second retractor blades assume a predefined orientation with respect to each other.

6. The tool of claim 5, wherein the blade portions of the first and second retractor blades form an angle of about 90° with one another in the predefined orientation.

7. The tool of claim 4, wherein the first and second retractor blades are pivotably connectable to the first and second arms, respectively, such that each of the first and second retractor blades can pivot only in a single plane.

8. The tool of claim 4, wherein each of the first and second arms comprises a first arm portion and a second arm portion that are movable relative to one another.

9. The tool of claim 8, wherein the first and second arm portions of each of the first and second arms are configured to assume a first configuration where the first and second arm portions are aligned with each other, and a second configuration where the first and the second arm portions are angled with respect to each other.

10. The tool of claim 8, wherein the first and second arm portions of each of the first and second arms are rotatable relative to one another.

11. The tool of claim 8, wherein the first and second arm portions of each of the first and second arms are lockable relative to each other.

12. The tool of claim 4, wherein the first and second arms are movable relative to each other on the frame.

13. The tool of claim 12, wherein the first arm is movably mounted to the frame and the second arm is fixedly mounted to the frame.

14. The tool of claim 12, wherein the frame comprises a positioning rod along which the first arm is incrementally and/or continuously movable.

15. The tool of claim 4, further comprising a third retractor blade mountable to the frame, wherein the third retractor blade comprises a blade portion that is arranged opposite to blade portions of the first and second retractor blades and is movable in a direction perpendicular to a direction of displacement between the first arm and the second arm on the frame.

16. An instrument configured to attach to a bone anchoring element during surgery, the instrument comprising:
an elongate portion;
an end portion located at an end of the elongate portion, the end portion defining an opening having a first section sized to permit insertion and removal of a head of the bone anchoring element therethrough, and a second section forming a seat that defines at least part of a circular profile sized to prevent removal of the head through the opening when the head is held in the seat; and
a spring portion configured to urge the head from the first section of the opening towards the second section of the opening, wherein the spring portion remains spaced apart from the circular profile defined by the seat and from the head when the head is held in the seat.

17. The instrument of claim 16, wherein the spring portion comprises a leaf spring attachable to the elongate portion.

* * * * *